United States Patent [19]

Debono et al.

[11] Patent Number: 4,629,786

[45] Date of Patent: Dec. 16, 1986

[54] C-20- AND C-23 MODIFIED MACROLIDE DERIVATIVES

[75] Inventors: Manuel Debono; Herbert A. Kirst, both of Indianapolis, Ind.

[73] Assignee: Eli Lilly and Company, Indianapolis, Ind.

[21] Appl. No.: 614,343

[22] Filed: May 25, 1984

Related U.S. Application Data

[63] Continuation-in-part of Ser. No. 470,833, Feb. 28, 1983, abandoned.

[51] Int. Cl.$^4$ ............................................. C07H 17/08
[52] U.S. Cl. ................................................... 536/7.1
[58] Field of Search ..................................... 536/7.1

[56] References Cited

U.S. PATENT DOCUMENTS

| | | | |
|---|---|---|---|
| 3,459,853 | 8/1969 | Gorman et al. | 424/121 |
| 4,196,280 | 4/1980 | Umezawa et al. | 536/17 R |
| 4,279,896 | 7/1981 | Ganguly et al. | 424/180 |
| 4,304,856 | 12/1981 | Baltz et al. | 435/76 |
| 4,321,361 | 3/1982 | Baltz et al. | 536/17 R |
| 4,321,362 | 3/1982 | Baltz et al. | 536/17 R |
| 4,345,069 | 8/1982 | Sakakibara et al. | 536/7.1 |
| 4,396,613 | 8/1983 | Kirst | 424/180 |
| 4,401,660 | 8/1983 | Kirst | 424/180 |
| 4,438,109 | 3/1984 | Umezawa et al. | 536/7.1 |
| 4,440,759 | 4/1984 | Omura et al. | 424/180 |
| 4,443,436 | 4/1984 | Kirst et al. | 424/180 |
| 4,452,784 | 6/1984 | Kirst et al. | 424/180 |
| 4,459,290 | 7/1984 | Kirst et al. | 424/180 |

FOREIGN PATENT DOCUMENTS

| | | |
|---|---|---|
| 0033433 | 8/1981 | European Pat. Off. |
| 56-122397 | 9/1981 | Japan . |
| 2081711 | 2/1982 | United Kingdom . |

OTHER PUBLICATIONS

H. Matsubara et al., "Chemical Transformation of Tylosin, a 16-Membered Macrolide, and Its Structure-Activity Relationship", *Chem. Pharm. Bull.* 30 (1), 97-110 (1982).

S. Omura et al., "Novel Dimeric Derivatives of Leucomycins and Tylosin, Sixteen-Membered Macrolides", *J. Med. Chem.* 25, 271-275 (1982).

Derwent Abstract No. 71396Y of Japanese Unexamined Patent 2100-485 (Takeda), Aug. 23, 1977.

A. Tanaka et al., "Syntheses of 4'-Deoxy-Demycarosyl Tylosin and Its Analogues", *J. Antibiotics* 34 (10), 1381-1384 (1981).

S. Satoi et al., "Mycinamicins, New Macrolide Antibiotics. I: Taxonomy, Production, Isolation, Characterization and Properties", *J. Antibiotics* 33 (4), 364-377 (1980).

A. Tanaka et al., "Syntheses of 23-Dialkylamino Derivatives of Mycaminosyl Tylonolide and 4'-Deoxymycaminosyl Tylonolide Effective Against Gram-Negative Bacteria", *J. Antibiotics* 35 (1), 113-116 (1982).

A. Tanaka et al., "Synthesis of 4'-Deoxymycaminosyl Tylonolide", *J. Antibiotics* 34 (10), 1374-1376 (1981).

A. Tanaka et al., "Synthesis of Derivatives of 4'-Deoxymycaminosyl Tylonolide and Mycaminosyl Tylonolide Modified at C-23", *J. Antibiotics* 34 (10), 1377-1380 (1981).

Derwent Abstract No. 92092A/51 of Japanese Unexamined Patent 3130-686, (Toyo Brewing), Nov. 14, 1978.

Derwent Abstract No. 008688/01 of Japanese Unexamined Patent 3132-584, (Toyo Brewing), Nov. 18, 1978.

Derwent Abstract No. 65537B/36 of Japanese Unexamined Patent 4095-584, (Toyo Brewing), Jul. 28, 1979.

Derwent Abstract No. 83-10173K of European Patent 70-170 (Zh Biseibutsu Kogaku Ken), Jan. 19, 1983.

*Primary Examiner*—Johnnie R. Brown
*Assistant Examiner*—Elli Peselev
*Attorney, Agent, or Firm*—Nancy J. Harrison

[57] ABSTRACT

C-20-Modified derivatives of macrolide antibiotics which include demycinosyltylosin (DMT), 20-dihydro-23-demycinosyltylosin (dihydro-DMT), 23-de(-mycinosyloxy)tylosin (DMOT), 20-dihydro-23-de(-mycinosyloxy)tylosin (dihydro-DMOT), 5-O-mycaminosyltylonolide (OMT), 20-dihydro-5-O-mycaminosyltylonolide (dihydro-OMT), 23-deoxy-5-O-mycaminosyltylonolide (DOMT), and 20-dihydro-23-deoxy-5-O-mycaminosyltylonolide (dihydro-DOMT) inhibit pathogenic bacteria, especially gram-positive bacteria, and Mycoplasma species; and pharmaceutical compositions thereof.

23 Claims, No Drawings

C-20- AND C-23 MODIFIED MACROLIDE DERIVATIVES

CROSS REFERENCE TO RELATED APPLICATION

This application is a continuation-in-part of copending application Ser. No. 470,833, filed Feb. 28, 1983, now abandoned, Aug. 15, 1984.

SUMMARY OF THE INVENTION

This invention relates to C-20- and C-23-modified macrolide derivatives having formula 1:

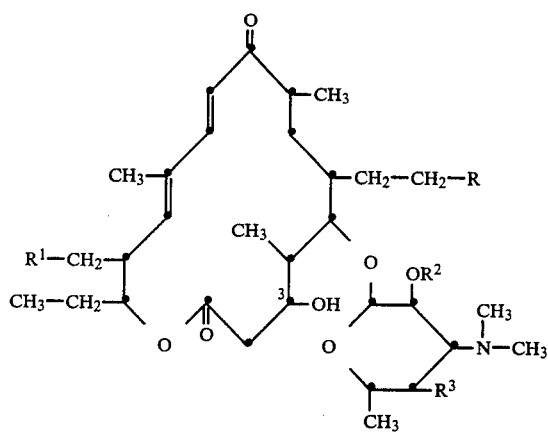

wherein:

R is (i) a saturated or unsaturated secondary amino group of the formula

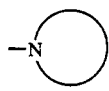

in which the nitrogen atom is part of an otherwise carbocyclic ring system selected from a monocyclic ring containing from 5 to 16 ring atoms or a bicyclic or tricyclic ring system containing from 8 to 20 ring atoms wherein one or more of the carbon atoms may be substituted by $C_1$-$C_4$ alkyl, $C_2$-$C_4$ alkenyl, $C_2$-$C_4$ alkynyl, $C_1$-$C_4$ alkoxy, $C_1$-$C_4$ alkoxycarbonyl, hydroxyl, $C_1$-$C_4$ alkanoyloxy, halo, halo-$C_1$-$C_4$ alkyl, $-N(C_1$-$C_4$ alkyl$)_2$, $-N(CH_2)_m$,

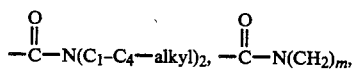

cyano, ethylenedioxy, benzyl, phenyl, or phenyl substituted by from 1 to 3 substituents selected from nitro, halo, $C_1$-$C_4$-alkyl, $C_1$-$C_4$ alkoxy, hydroxy, amino, or mono- or di-($C_1$-$C_4$ alkyl)amino; and m is an integer from 4 through 7; or (ii) a monocyclic saturated or unsaturated nitrogen-containing heterocyclic ring bonded through the nitrogen atom, said ring having (1) from 5 to 7 ring atoms which include up to 3 additional heteroatoms selected from nitrogen, oxygen and sulfur, and (2) up to 3 substituent groups selected from methyl, ethyl and phenyl;

$R^1$ is (i) hydrogen or $-OH$;

(ii) chloro, fluoro, bromo, iodo, $-OAr$, $-O-$tetrahydrofuranyl, $-O-$tetrahydropyranyl, $-SR^5$, azido, $-NR^6R^7$, or N-phthalimido;

(iii) a saturated or unsaturated secondary amino group of the formula

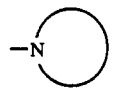

in which the nitrogen atom is part of an otherwise carbocyclic ring system selected from a monocyclic ring containing from 5 to 16 ring atoms or a bicyclic or tricyclic ring system containing from 8 to 20 ring atoms wherein one or more of the carbon atoms may be substituted by $C_1$-$C_4$ alkyl, $C_2$-$C_4$ alkenyl, $C_2$-$C_4$ alkynyl, $C_1$-$C_4$ alkoxy, $C_1$-$C_4$ alkoxycarbonyl, hydroxyl, $C_1$-$C_4$ alkanoyloxy, halo, halo-$C_1$-$C_4$ alkyl, $-N(C_1$-$C_4$ alkyl$)_2$, $-N(CH_2)_m$,

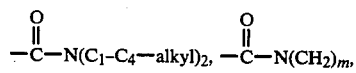

cyano, ethylenedioxy, benzyl, phenyl, or phenyl substituted by from 1 to 3 substituents selected from nitro, halo, $C_1$-$C_4$-alkyl, $C_1$-$C_4$ alkoxy, hydroxy, amino, or mono- or di-($C_1$-$C_4$ alkyl)amino; or (iv) a monocylic saturated or unsaturated nitrogen-containing heterocyclic ring bonded through the nitrogen atom, said ring having (1) from 5 to 7 ring atoms which include up to 3 additional heteroatoms selected from nitrogen, oxygen and sulfur, and (2) up to 3 substituent groups selected from methyl, ethyl and phenyl;

$R^2$ is hydrogen, optionally substituted $C_1$-$C_5$-alkanoyl or optionally substituted benzoyl, phenylacetyl or phenylpropionyl;

$R^3$ is hydrogen, hydroxy; optionally substituted $C_1$-$C_5$-alkanoyloxy; optionally substituted benzoyloxy, phenylacetoxy or phenylpropionyloxy; or

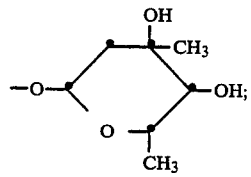

(mycarosyloxy)

Ar is (i) phenyl, derivatized phenyl, or naphthyl;

(ii) an optionally substituted heteroaryl group selected from pyridinyl, pyrimidinyl, pyridazinyl, pyrazinyl, triazinyl, indolyl, isoquinolinyl, quinolinyl, quinazolinyl, cinnolinyl, quinoxalinyl, phthalazinyl, benzotriazolyl, benzoxazolyl, benzimidazolyl, carbazolyl, or acridinyl;

(iii) optionally substituted $C_1$-$C_5$-alkanoyl; optionally substituted benzoyl, phenylacetyl, phenylpropionyl, phenoxyacetyl or phenylthioacetyl; methanesulfonyl; trifluoromethanesulfonyl; or optionally substituted phenylsulfonyl;

$R^5$ is optionally substituted $C_1$–$C_4$-alkyl; cyclohexyl; optionally substituted phenyl, benzyl or phenethyl; or an optionally substituted heteroaryl group selected from imidazolyl, pyrazolyl, pyridinyl, pyrimidinyl, pyrazinyl, pyridazinyl, triazinyl, triazolyl, tetrazolyl, oxazolyl, isoxazolyl, oxadiazolyl, thiazolyl, isothiazolyl, thiadiazolyl, thienyl and furanyl;

$R^6$ is hydrogen, optionally substituted $C_1$–$C_6$-alkyl, phenyl, benzyl, phenethyl or $C_3$–$C_8$-cycloalkyl; and $R^7$ is an $R^6$ group or optionally substituted $C_1$–$C_5$-alkanoyl, optionally substituted benzoyl, phenylacetyl, phenylpropionyl, phenoxyacetyl or phenylthioacetyl, or alkoxycarbonyl;

provided that (1) when $R^1$ is —$NHR^6$, $R^2$ must be hydrogen, $R^3$ must be hydrogen, hydroxy or mycarosyloxy, and Ar cannot be a type (iii) substituent; and (2) when $R^2$ is hydrogen, $R^3$ must be hydrogen, hydroxy or mycarosyloxy; and their salts, particularly the acid addition salts, of these compounds.

The compounds of this invention are useful as antibiotics and/or as intermediates to antibiotics. This invention also relates to pharmaceutical compositions comprising these compounds and to methods of treatment wherein these compounds or compositions are administered to obtain an antibiotic effect or to enhance growth promotion in animals.

DETAILED DESCRIPTION OF THE INVENTION

This invention relates to new antibiotics. In particular, this invention relates to a group of C-20- and C-23-modified macrolide derivatives and to their salts, particularly the acid addition salts. This invention also relates to methods of treating certain infections with, and pharmaceutical compositions comprising, the specified derivatives and their pharmaceutically acceptable acid addition salts.

New, improved antibiotics are continually in demand. In addition to antibiotics which are useful for treating human diseases, improved antibiotics are also needed in the veterinary field. Increased potency, expanded spectrum of bacterial inhibition, increased in vivo efficacy, and improved pharmaceutical properties (such as greater oral absorption, higher blood or tissue concentrations, longer body half life, and more advantageous rate or route of excretion and rate or pattern of metabolism) are some of the goals for improved antibiotics.

The derivatives of this invention are compounds of formula 1:

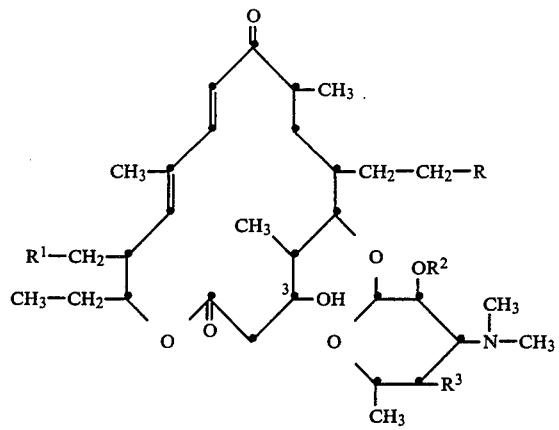

wherein
R is
(i) a saturated or unsaturated secondary amino group of the formula

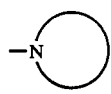

in which the nitrogen atom is part of an otherwise carbocyclic ring system selected from a monocyclic ring containing from 5 to 16 ring atoms or a bicyclic or tricyclic ring system containing from 8 to 20 ring atoms wherein one or more of the carbon atoms may be substituted by $C_1$–$C_4$ alkyl, $C_2$–$C_4$ alkenyl, $C_2$–$C_4$ alkynyl, $C_1$–$C_4$ alkoxy, $C_1$–$C_4$ alkoxycarbonyl, hydroxyl, $C_1$–$C_4$ alkanoyloxy, halo, halo-$C_1$–$C_4$ alkyl, —$N(C_1$–$C_4$ alkyl$)_2$, —$N(CH_2)_m$,

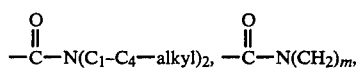

cyano, ethylenedioxy, benzyl, phenyl, or phenyl substituted by from 1 to 3 substituents selected from nitro, halo, $C_1$–$C_4$-alkyl, $C_1$–$C_4$ alkoxy, hyroxy, amino, or mono- or di-($C_1$–$C_4$ alkyl)amino; and m is an integer from 4 through 7; or (ii) a monocyclic saturated or unsaturated nitrogen-containing heterocyclic ring bonded through the nitrogen atom, said ring having (1) from 5 to 7 ring atoms which include up to 3 additional heteroatoms selected from nitrogen, oxygen and sulfur, and (2) up to 3 substituent groups selected from methyl, ethyl and phenyl;

$R^1$ is
(i) hydrogen or —OH;
(ii) chloro, fluoro, bromo, iodo, —OAr, —O—tetrahydrofuranyl, —O—tetrahydropyranyl, —$SR^5$, azido, —$NR^6R^7$, or N-phthalimido;
(iii) a saturated or unsaturated secondary amino group of the formula

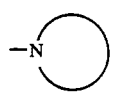

in which the nitrogen atom is part of an otherwise carbocyclic ring system selected from a monocyclic ring containing from 5 to 16 ring atoms or a bicyclic or tricyclic ring system containing from 8 to 20 ring atoms wherein one or more of the carbon atoms may be substituted by $C_1$-$C_4$ alkyl, $C_2$-$C_4$ alkenyl, $C_2$-$C_4$ alkynyl, $C_1$-$C_4$ alkoxy, $C_1$-$C_4$ alkoxycarbonyl, hydroxyl, $C_1$-$C_4$ alkanoyloxy, halo, halo-$C_1$-$C_4$ alkyl, —N($C_1$-$C_4$ alkyl)$_2$, —N(CH$_2$)$_m$,

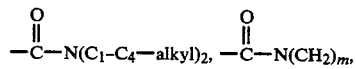

cyano, ethylenedioxy, benzyl, phenyl, or phenyl substituted by from 1 to 3 substituents selected from nitro, halo, $C_1$-$C_4$-alkyl, $C_1$-$C_4$ alkoxy, hydroxy, amino, or mono- or di-($C_1$-$C_4$ alkyl)amino; or (iv) a monocyclic saturated or unsaturated nitrogen-containing heterocyclic ring bonded through the nitrogen atom, said ring having (1) from 5 to 7 ring atoms which include up to 3 additional heteroatoms selected from nitrogen, oxygen and sulfur, and (2) up to 3 substituent groups selected from methyl, ethyl and phenyl;

$R^2$ is hydrogen, optionally substituted $C_1$-$C_5$-alkanoyl or optionally substituted benzoyl, phenylacetyl or phenylpropionyl;

$R^3$ is hydrogen, hydroxy; optionally substituted $C_1$-$C_5$-alkanoyloxy; optionally substituted benzoyloxy, phenylacetoxy or phenylpropionyloxy; or

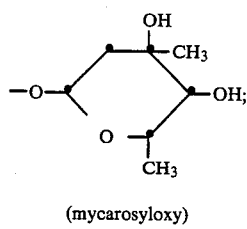

(mycarosyloxy)

Ar is (i) phenyl, derivatized phenyl, or naphthyl;
(ii) an optionally substituted heteroaryl group selected from pyridinyl, pyrimidinyl, pyridazinyl, pyrazinyl, triazinyl, indolyl, isoquinolinyl, quinolinyl, quinazolinyl, cinnolinyl, quinoxalinyl, phthalazinyl, benzotriazolyl, benzoxazolyl, benzimidazolyl, carbazolyl, or acridinyl;
(iii) optionally substituted $C_1$-$C_5$-alkanoyl; optionally substituted benzoyl, phenylacetyl, phenylpropionyl, phenoxyacetyl or phenylthioacetyl; methanesulfonyl; trifluoromethanesulfonyl; or optionally substituted phenylsulfonyl;

$R^5$ is optionally substituted $C_1$-$C_4$-alkyl; cyclohexyl; optionally substituted phenyl, benzyl or phenethyl; or an optionally substituted heteroaryl group selected from imidazolyl, pyrazolyl, pyridinyl, pyrimidinyl, pyrazinyl, pyridazinyl, triazinyl, triazolyl, tetrazolyl, oxazolyl, isoxazolyl, oxadiazolyl, thiazolyl, isothiazolyl, thiadiazolyl, thienyl and furanyl;

$R^6$ is hydrogen, optionally substituted $C_1$-$C_6$-alkyl, phenyl, benzyl, phenethyl or $C_3$-$C_8$-cycloalkyl; and $R^7$ is an $R^6$ group or optionally substituted $C_1$-$C_5$-alkanoyl, optionally substituted benzoyl, phenylacetyl, phenylpropionyl, phenoxyacetyl or phenylthioacetyl, or alkoxycarbonyl;

provided that (1) when $R^1$ is —NHR$^6$, $R^2$ must be hydrogen, $R^3$ must be hydrogen, hydroxy or mycarosyloxy, and Ar cannot be a type (iii) substituent; and (2) when $R^2$ is hydrogen, $R^3$ must be hydrogen, hydroxy or mycarosyloxy; and the salts, particularly the acid addition salts, of these compounds.

When R is unsaturated, representative groups are 1,2,3,6-tetrahydropyridin-1-yl; 1,2,3,4-tetrahydroquinolin-1-yl; 1,2,3,4-tetrahydroisoquinolin-2-yl; indol-1-yl; isoindol-2-yl; indolin-1-yl; isoindolin-2-yl; 2,3,4,5-tetrahydro-1H-1-benzazepin-1-yl; 2,3,4,5-tetrahydro-1H-2-benzazepin-2-yl; 2,3,4,5-tetrahydro-1H-3-benzazepin-3-yl; pyrrol-1-yl; 1H-azepin-1-yl; carbazol-9-yl; acridin-10-yl; and acridin-9-one-10-yl.

When R is a saturated monocylic ring, representative groups include pyrrolidin-1-yl, piperidin-1-yl, hexahydroazepin-1-yl, octahydroazocin-1-yl, octahydro-1H-azonin-1-yl, azacyclotridecan-1-yl and the like.

When R is a saturated bicyclic or tricyclic ring, representative groups include decahydroquinolin-1-yl; decahydroisoquinolin-2-yl; decahydrocyclohepta[b]-pyrrol-1-yl; decahydrocyclohepta[c]pyrrol-2-yl; decahydrocyclopent[c]azepin-2-yl; decahydrocyclopent[d]azepin-3-yl; an azabicycloheptanyl group such as 3-azabicyclo[3.2.0]heptan-3-yl; an azabicyclooctanyl such as 6-azabicyclo[3.2.1]octan-6-yl; an azabicyclononanyl group such as 3-azabicyclo[3.2.2]nonan-3-yl; an azabicyclodecanyl group such as 4-azabicyclo[5.3.0]decan-4-yl; an azatricyclogroup such as 2-azatricyclo[6.2.2.2$^{3,6}$]tetradcan-2-yl or dodecahydrocarbazol-9-yl; and a spiro-fused system such as 1-azaspiro[4.5]decan-1-yl.

Representative groups when R has one or more substituents on the carbon atoms of the ring system include 1,3,3-trimethyl-6-azabicyclo[3.2.1]-octan-6-yl; 4-piperidinopiperidin-1-yl; 3,5-dimethylpiperidin-1-yl; 3,3,5-trimethylhexahydroazepin-1-yl; 4-phenylpiperidin-1-yl; 3-(N,N-diethylcarbamonyl)piperidin-1-yl; and the like.

The term "$C_1$-$C_5$-alkanoyl" as used herein means an acyl moiety derived from a carboxylic acid containing from one to five carbon atoms. In such a moiety, the alkyl group can be straight, branched, or cyclic. When optionally substituted, the alkyl group can bear one to three halo substituents. Halo substituents are selected from the group consisting of Cl, Br and F. Acetyl, chloroacetyl, trichloroacetyl, trifluoroacetyl, propionyl, n-butyryl, isobutyryl, n-valeryl, and isovaleryl are examples of such groups. The term "$C_1$-$C_5$-alkanoyloxy" refers to the corresponding acyloxy moiety.

The terms "optionally substituted benzoyl, phenylacetyl, phenylpropionyl, phenoxyacetyl or phenylthioacetyl", "optionally substituted benzoyl, phenylacetyl or phenylpropionyl", "optionally substituted benzoyloxy, phenylacetoxy or phenylpropionyloxy", "optionally substituted phenyl, benzyl or phenethyl", "optionally substituted benzyl, phenethyl or phenoxyethyl" and "optionally substituted phenylsulfonyl" mean that the phenyl portion of the moiety is optionally substituted by from one to five halo or methyl groups or by from one to two methoxyl, nitro or hydroxyl groups.

The term "derivatized phenyl" refers to a phenyl group which has from one to five halo, methoxyl or $C_1$–$C_4$-alkyl substituents, or from one to two nitro, amino, methylamino, ethylamino, dimethylamino, diethylamino, $C_4$–$C_{10}$-methyleneamino, azido, hydroxy, hydroxymethyl, aminomethyl, (methylamino)methyl, (ethylamino)methyl, (dimethylamino)methyl, (diethylamino)methyl, ($C_4$–$C_{10}$-methyleneamino)methyl, formyl, acetyl, benzoyl, methoxycarbonyl, ethoxycarbonyl, carboxamido, N-methylcarboxamido, N,N'-dimethylcarboxamido, cyano, phenyl, phenoxy or benzyl substituents.

The term "optionally substituted heteroaryl group" as used herein means that the heteroaryl group may have at least one suitable substituent(s) such as a $C_1$–$C_4$-alkyl, halo, methoxy, ethoxy, hydroxy (or the keto tautomer) or phenyl group.

The terms "$C_1$–$C_3$-alkyl", "$C_1$–$C_4$-alkyl" or "$C_1$–$C_6$-alkyl" as used herein mean a straight- or branched-chain alkyl group containing the specified number of carbon atoms. Such groups include methyl, ethyl, isopropyl, n-butyl, tert-butyl, n-hexyl, and the like. "Optionally substituted" $C_1$–$C_4$-alkyl or $C_1$–$C_6$-alkyl means that the alkyl group contains one or more fluoro or chloro substituents. By alkenyl or alkynyl are meant a hydrocarbon group containing a double or triple bond, respectively. "$C_3$–$C_8$-cycloalkyl" refers to a cycloalkyl group containing from three to eight carbon atoms. Examples of such groups are cyclopropyl, cyclohexyl and cyclooctyl.

The term "alkoxycarbonyl" represents a member of a group selected from t-butoxycarbonyl, methoxycarbonyl, ethoxycarbonyl, 2,2,2-trichloroethoxycarbonyl, phenoxycarbonyl and benzyloxycarbonyl.

The term "$C_4$–$C_{10}$-methyleneamino" represents a cyclic amino substituent of the formula —N(CH$_2$)$_n$ wherein n is an integer from four to ten. Pyrrolidinyl, piperidinyl, and octahydroazocinyl are examples of such groups.

The modified macrolide derivatives of this invention are prepared from the group of macrolide antibiotics which includes demycinosyltylosin (DMT), 20-dihydro-23-demycinosyltylosin (dihydro-DMT), 23-de(-mycinosyloxy)tylosin (DMOT), 20-dihydro-23-de(-mycinosyloxy)tylosin (dihydro-DMOT), 5-O-mycaminosyltylonolide (OMT), 20-dihydro-5-O-mycaminosyltylonolide (dihydro-OMT), 23-deoxy-5-O-mycaminosyltylonolide (DOMT), and 20-dihydro-23-deoxy-5-O-mycaminosyltylonolide (dihydro-DOMT).

DMT, dihydro-DMT, DMOT, dihydro-DMOT, DOMT, and dihydro-DMOT are antibiotics described by Richard H. Baltz, Gene M. Wild, and Eugene T. Seno in U.S. Pat. Nos. 4,321,361 and 4,321,362, both of which issued on Mar. 23, 1982. OMT and dihydro-OMT are described by Marvin Gorman and Robert D. Morin in U.S. Pat. No. 3,459,853, issued on Aug. 5, 1969.

The structures of the starting antibiotics are shown in formulas 2-9:

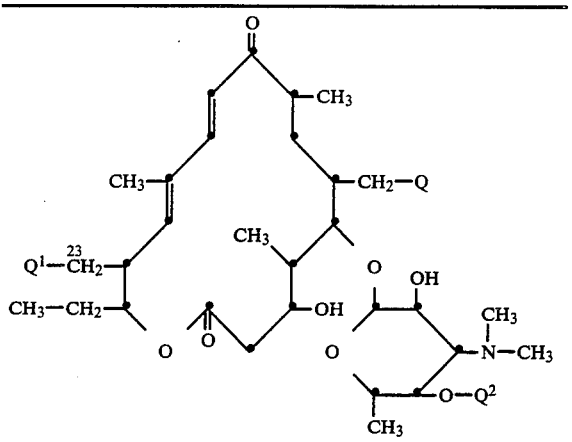

| | Q | $Q^1$ | $Q^2$ |
|---|---|---|---|
| 2 DMT: | —CHO | —OH | mycarosyl |
| 3 dihydro-DMT: | —CH$_2$OH | —OH | " |
| 4 OMT: | —CHO | —OH | H |
| 5 dihydro-OMT: | —CH$_2$OH | —OH | H |
| 6 DMOT: | —CHO | H | mycarosyl |
| 7 dihydro-DMOT: | —CH$_2$OH | H | " |
| 8 DOMT: | —CHO | H | H |
| 9 dihydro-DOMT: | —CH$_2$OH | H | H |

The formula 1 compounds are often prepared by initially modifying the starting antibiotic at the C-20 position. Preparation of the C-20-modified derivatives involves in a formal sense reductive amination of the C-20 aldehyde group of DMT, OMT, DMOT, or DOMT. This can be accomplished by two methods.

METHOD 1

In this method, the aldehyde group of compound 2, 4, 6 or 8 is first reduced to give the corresponding 20-dihydro compounds, i.e. the compound of formula 3, 5, 7 or 9. The C-20 hydroxyl group in these compounds is then converted to a leaving group suitable for displacement reactions by one of two methods. In one method the C-20 hydroxyl group is converted to the trifluoromethanesulfonyl (triflate) group, which may be further converted to an iodo group, if desired. In the other method, which can only be used with OMT and DOMT, the iodo derivative is directly formed by addition of iodine (dissolved in a suitable solvent such as dimethylformamide) to a solution of the 20-dihydro derivative and triphenylphosphine under an inert atmosphere.

The leaving group at C-20 (iodo, triflate, etc.) is then displaced by reaction with the appropriate amine in a suitable solvent, such as acetonitrile, until the desired 20-modified derivative is formed.

It should be noted that, when the compounds of formulas 3 or 5 are used as starting materials, two primary hydroxyl groups are present which react in a similar manner. The primary hydroxyl group at C-20, however, is usually replaced more rapidly than the hydroxyl group at C-23. Although many of the procedures described supra give mixtures of 20-monosubstituted derivatives and 20,23-disubstituted derivatives, such mixtures can be readily separated by techniques known in the art, such as, for example, chromatography using silica gel as the adsorbent. Formation of C-20-monosubstituted derivatives may be optimized by not carrying the reaction to completion, for example, by using less than two molar equivalents of reactant(s). Conversely, when C-20, C-23-disubstituted derivatives are sought, the reaction should be carried to completion and two molar equivalents or an excess of reactant(s) should be used.

METHOD 2

In this method, the aldehyde group of compound 2, 4, 6 or 8 is reacted directly with the corresponding amine in the presence of a suitable reducing agent in an appropriate solvent until the desired product is formed. Sodium cyanoborohydride is an example of a suitable reducing agent, and anhydrous methanol is a useful solvent for this reaction. The reaction may be carried out under an inert atmosphere, but this is usually not required. With less reactive amines, more forcing conditions for forming the intermediate iminium complex between the macrolide and amine may be required, e.g. heating, use of a drying agent or water scavenger or heating under conditions of azeotropic removal of water in solvents such as benzene or toluene.

Compounds wherein the substituent $R^1$ differs from the substituent R may also be prepared by modifying the hydroxyl group at C-23 before reducing the aldehyde at C-20. Procedures for modifying the C-23 position are provided in copending applications Ser. Nos. 399,656 and 399,657, filed July 16, 1982, which are incorporated herein by reference. In addition, the diethyl azodicarboxylate/triphenylphosphine (DEAD) reaction may conveniently be used to prepare many of the C-23-modified compounds [see O. Mitsunobu, *Synthesis* 1(1) 1–28 (1981)]. This procedure for modification of primary hydroxyl groups is discussed further in application Ser. No. 417,248, filed Sept. 13, 1982. Other procedures for modification of the C-23-position are described by A. Tanaka et al. in *J. Antibiotics* 35 (1) 113–116, (1982). Procedures for the preparation of 23-esters are discussed in copending applications Ser. Nos. 330,341, 330,294 and 330,295, all of which were filed Dec. 14, 1981, and by Tanaka, et al., in *J. Antibiotics* 34 (10), 1377–1379 (1981).

An alternate method for preparing compounds with different substituents at C-20 and C-23 is to modify the C-20 position of a macrolide not having a free C-23 hydroxyl group. One example of this approach is to prepare a C-20-modified derivative of desmycosin, tylosin, macrocin, lactenocin, demethylmacrocin and demethyllactenocin, as described in our application Ser. No. 417,247, filed Sept. 13, 1982, followed by hydrolysis of the neutral sugar(s), using procedures known in the art (see, for example, U.S. Pat. No. 3,459,853). By this procedure, a 20-modified derivative of OMT can be selectively prepared, which in turn can be modified at the C-23 position, as discussed supra.

Use of a protecting group for the hydroxyl group at C-23 of OMT and DMT prior to reduction of the aldehyde also permits selective modification of C-20. Removal of the protecting group after appropriate modification of C-20 yields C-20-modified derivatives having a hydroxyl group at C-23, which may then be modified as outlined previously. Examples of useful protecting groups are groups such as tetrahydropyranyl and tetrahydrofuranyl. The tetrahydropyranyl and tetrahydrofuranyl protecting groups are described, for example, by Tanaka et al., supra.

The modified derivatives of OMT and DOMT can also be prepared by acidic hydrolysis of mycarose from the corresponding modified derivatives of DMT and DMOT, respectively, prepared by the methods previously described. Procedures for the acidic hydrolysis of mycarose from DMT and DMOT to form OMT and DOMT, respectively, are found in U.S. Pat. Nos. 4,321,361 and 4,321,362.

The 4'-deoxy derivatives of this invention, i.e. the compounds of formula 1 when $R^3$ is hydrogen, are readily prepared by procedures analogous to those described supra, using 4'-deoxy-OMT or 4'-deoxy-DOMT as the starting material. These starting materials can be prepared via procedures outlined in *J. Antibiotics* 34, 1381–1384 (1981). Alternatively, deoxygenation at 4' may be accomplished in OMT or DOMT subsequent to modification of the C-20 and/or C-23 positions.

The formula 1 compounds which are ester derivatives are prepared by esterifying the respective C-20 and/or C-23-modified derivative on the 2', 4', and/or 23-hydroxyl groups (when present) by treatment with acylating agents, using standard methods exemplified in the art. The preparation of 2'-O-ester derivatives of the C-20- and/or C-23-modified derivatives is accomplished by procedures similar to those described by Baltz et al. in U.S. Pat. Nos. 4,321,361 and 4,321,362. Esterification of the 2', 4' and/or 23-hydroxyl groups of these modified derivatives may be accomplished by acylation of the hydroxyl groups using similar procedures as outlined in the previously discussed applications Ser. Nos. 330,341, 330,295, and 330,294.

The C-20-modified derivatives of this invention form salts, particularly acid addition salts. These acid addition salts are also useful as antibiotics and are a part of this invention. In another aspect, such salts are useful as intermediates, for example, for separating and purifying the derivatives. In addition, the salts have an improved solubility in water.

Representative suitable salts include those salts formed by standard reactions with both organic and inorganic acids such as, for example, sulfuric, hydrochloric, phosphoric, acetic, succinic, citric, lactic, maleic, fumaric, palmitic, cholic, pamoic, mucic, D-glutamic, d-camphoric, glutaric, glucolic, phthalic, tartaric, formic, lauric, stearic, salicylic, methanesulfonic, benzenesulfonic, sorbic, picric, benzoic, cinnamic, and like acids.

Pharmaceutically acceptable acid addition salts are an especially preferred group of salts of this invention.

A preferred group of compounds of this invention are the formula 1 compounds wherein R is a saturated monocyclic ring. In this group, those compounds wherein R is hexahydroazepin-1-yl octahydroazocin-1-yl, 3,5-di-methylpiperidin-1-yl and 4-phenylpiperidin-1-yl are especially preferred.

Another preferred group are the formula 1 compounds wherein R is a bicyclic ring system. In this group, those compounds wherein R is azabicycloalkanyl, particularly azabicyclononanyl, are especially preferred.

Yet another preferred group of compounds of this invention are the formula 1 compounds wherein $R^1$ is a group (iii) substituent or an —OAr substituent. Still another group of formula 1 compounds are those wherein $R^3$ is hydrogen or hydroxy.

Illustrative formula 1 compounds of this invention are listed in Table I.

TABLE I
Illustrative Formula 1 Compounds

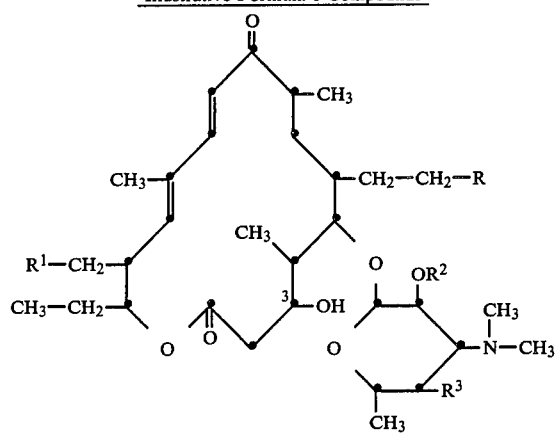

| Compound No. | R | R¹ | R² | R³ |
|---|---|---|---|---|
| 1 | pyrrolidin-1-yl | OH | H | —OH |
| 2 | piperidin-1-yl | " | " | " |
| 3 | 4-hydroxypiperidin-1-yl | " | " | " |
| 4 | 4-phenylpiperidin-1-yl | " | " | " |
| 5 | hexahydroazepin-1-yl | " | " | " |
| 6 | octahydroazocin-1-yl | " | " | " |
| 7 | octahydro-1H—azonin-1-yl | " | " | " |
| 8 | decahydroazecin-1-yl | " | " | " |
| 9 | azacycloundecan-1-yl | " | " | " |
| 10 | azacyclotridecan-1-yl | " | " | " |
| 11 | 1,2,3,4-tetrahydroquinolin-1-yl | " | " | " |
| 12 | 1,2,3,4-tetrahydroisoquinolin-2-yl | " | " | OH |
| 13 | 3-azabicyclononan-3-yl | " | " | " |
| 14 | morpholino | " | " | " |
| 15 | octahydroazocin-1-yl | octahydroazocin-1-yl | " | " |
| 16 | 3-azabicyclononan-3-yl | octahydroazocin-1-yl | " | " |
| 17 | 3-azabicyclononan-3-yl | O—phenyl | " | " |
| 18 | morpholino | S—phenyl | " | " |
| 19 | octahydroazocin-1-yl | azido | " | " |
| 20 | octahydroazocin-1-yl | 3-azabicyclononan-3-yl | " | " |
| 21 | octahydroazocin-1-yl | OH | " | H |
| 22 | 3-azabicyclononan-3-yl | OH | " | H |
| 23 | hexahydroazepin-1-yl | H | " | OH |
| 24 | morpholino | H | " | " |
| 25 | 3-azabicyclononan-3-yl | OH | acetyl | acetoxy |
| 26 | 3,5-dimethylpiperidin-1-yl | OH | H | OH |
| 27 | 3,5-dimethylpiperidin-1-yl | 3,5-dimethylpiperidin-1-yl | H | OH |
| 28 | 3,5-dimethylpiperidin-1-yl | OH | H | H |
| 29 | 3,4-dimethoxypiperidin-1-yl | OH | H | OH |
| 30 | 3-methylpiperidin-1-yl | OH | H | OH |

The derivatives of this invention inhibit the growth of pathogenic bacteria, especially gram-positive baceteria, and Mycoplasma species. Certain of the derivatives are active against some gram-negative bacteria, such as Pasteurella species. The minimal inhibitory concentrations (MIC's) at which illustrative compounds inhibit certain bacteria are given in Table II. The MIC's in Table II were determined by standard agar-dilution assays.

TABLE II
Antibiotic Activity of Formula 1 Compounds[a]

| | Test Compound[b] | | | | | |
|---|---|---|---|---|---|---|
| Test Organism | 4 | 13 | 14 | 15 | 5 | 23 |
| Staphylococcus aureus X1.1 | 2 | 1 | 4 | 0.5 | 4 | 4 |
| Staphylococcus aureus V41[c] | 2 | 1 | 4 | 0.5 | 4 | 4 |
| Staphylococcus aureus X400[d] | 2 | 1 | 8 | 0.5 | 8 | 8 |
| Staphylococcus aureus S13E | 2 | 1 | 4 | 0.5 | 4 | 4 |
| Staphylococcus epidermidis EPI1 | 1 | 1 | 2 | 0.5 | 2 | 2 |
| Staphylococcus epidermidis EPI2 | 0.5 | 0.25 | 1 | 0.25 | 2 | 1 |
| Streptococcus pyogenes C203 | 2 | 2 | 1 | 0.125 | 0.5 | 0.5 |
| Streptococcus pneumoniae Park I | 0.25 | 0.25 | 0.5 | 0.125 | NT[h] | NT |
| Streptococcus pneumoniae Group D X66 | 2 | 4 | 4 | 0.5 | 16 | 8 |
| Streptococcus pneumoniae Group D X9960 | 4 | 8 | 4 | 1 | 16 | 16 |
| Haemophilus influenzae C.L.[e] | 8 | 4 | 16 | 0.5 | 16 | 16 |
| Haemophilus influenzae 76[f] | 8 | 2 | 4 | 1 | 16 | 16 |
| Escherichia coli EC14 | 32 | 32 | 128 | 4 | 128 | 128 |

TABLE II-continued

Antibiotic Activity of Formula 1 Compounds[a]

| Test Organism | Test Compound[b] | | | | | |
|---|---|---|---|---|---|---|
| | 4 | 13 | 14 | 15 | 5 | 23 |
| *Escherichia coli* TEM | 8 | 8 | 64 | 2 | 16 | 8 |
| *Klebsiella pneumoniae* X26 | 2 | 2 | 4 | 2 | 4 | 2 |
| *Klebsiella pneumoniae* KAE | 64 | 64 | —[g] | 8 | 128 | 128 |

[a]MIC in mcg/ml
[b]Compound numbers from Table I
[c]Penicillin-resistant strain
[d]Methicillin-resistant strain
[e]Ampicillin-sensitive strain
[f]Ampicillin-resistant strain
[g]Compound not active at 128 mcg/ml
[h]NT = not tested Some of the derivatives of this invention have shown in vivo antimicrobial activity against experimentally-induced infections in laboratory animals. When two doses of test compound were administered to mice experimentally infected with *S. pyogenes* C203, the activity observed was measured as an $ED_{50}$ value [effective dose in mg/kg to protect 50% of the test animals: see Warren Wick, et al., *J. Bacteriol.* 81, 233–235 (1961)]. $ED_{50}$ values observed for illustrtive compounds are given in Table III.

TABLE III $ED_{50}$ Values of Illustrative Formula 1 Compounds[a]

| | *Streptococcus pyogenes* C203 | |
|---|---|---|
| Test Compound[b] | Subcutaneous | Oral |
| 4 | >10 | >100 |
| 5 | 7.8 | >100 |
| 13 | 5.9 | 87 |
| 14 | >10 | >100 |
| 15 | >10 | >50 |
| 23 | >10 | >100 |

[a]mg/kg × 2; doses given 1 and 4 hours post-infection
[b]Compound numbers from Table I.

This invention also relates to methods of controlling infections caused by bacterial and mycoplasmal species. In carrying out the methods of this invention, an effective amount of a compound of formula 1a 1 is administered parenterally to an infected or susceptible warm-blooded animal.

The dose which is effective to control the infection will vary with the severity of the infection and the age, weight, and condition of the animal. The total dose required for protection parenterally will generally, however, be in the range of from about 1 to about 100 mg/kg and preferably will be in the range of from about 1 to about 50 mg/kg. The dose required for oral administration will generally be in the range of from 1 to about 300 mg/kg and preferably will be in the range of from about 1 to about 100 mg/kg. Suitable dosage regimens can be constructed.

In another aspect, this invention relates to compositions useful for the control of infections caused by bacteria and Mycoplasma species. These compositions comprise a compound of formula 1 together with a suitable vehicle. Compositions may be formulated for parenteral or oral administration by methods recognized in the pharmaceutical art.

Effective injectable compositions containing these compounds may be in either suspension or solution form. In the preparation of suitable formulations it will be recognized that, in general, the water solubility of the acid addition salts is greater than that of the free bases. Similarly, the bases are more soluble in dilute acids or in acidic solutions than in neutral or basic solutions.

In the solution form the compound is dissolved in a physiologically acceptable vehicle. Such vehicles comprise a suitable solvent, preservatives such as benzyl alcohol, if needed, and buffers. Useful solvents include, for example, water and aqueous alcohols, glycols, and carbonate esters such as diethyl carbonate. Such aqueous solutions contain, in general, no more than 50% of the organic solvent by volume.

Injectable suspension compositions require a liquid suspending medium, with or without adjuvants, as a vehicle. The suspending medium can be, for example, aqueous polyvinylpyrrolidone, inert oils such as vegetable oils or highly refined mineral oils, or aqueous carboxymethylcellulose.

Suitable physiologically acceptable adjuvants are necessary to keep the compound suspended in suspension compositions. The adjuvants may be chosen from among thickeners such as carboxymethylcellulose, polyvinylpyrrolidone, gelatin, and the aliginates. Many surfactants are also useful as suspending agents. Lecithin, alkylphenol polyethylene oxide adducts, naphthalenesulfonates, alkylbenzenesulfonates, and the polyoxyethylene sorbitan esters are useful suspending agents.

Many substances which affect the hydrophilicity, density, and surface tension of the liquid suspending medium can assist in making injectable suspensions in individual cases. For example, silicone antifoams, sorbitol, and sugars can be useful suspending agents.

In order to illustrate more fully the operation of this invention, the following examples are provided. In these examples the abbreviation "20-DH-DO" is used for the term "20-dihydro-20-deoxy".

EXAMPLE 1

20-DH-DO-20-[3-Azabicyclo(3.2.2)-nonan-3-yl]-OMT

OMT (3.0 g., 5.0 mmoles) was dissolved in anhydrous methanol (15 ml.). 3-Azabicyclo[3.2.2]-nonane (1.25 g., 10 moles) was dissolved in anhydrous methanol (15 ml.) and filtered to remove a white impurity. The filtrate was added to the OMT solution and the resulting solution was stirred for 5–10 minutes at room temperature in the presence of molecular sieves (3A). NaBH$_3$CN (0.63 g., 10 mmoles) was added, and the reaction was stirred at room temperature for 17 hours. The reaction mixture was filtered, and the filtrate was evaporated under vacuum to give a foam which was redissolved in ethyl acetate (150 ml.). The ethyl acetate solution was washed with water (150 ml.) and separated. A major portion of the product was then extracted from the ethyl acetate solution with 0.5M NaH$_2$PO$_4$ buffer (150 ml., pH 6.5).

The phosphate buffer solution was evaporated under vacuum to remove residual ethyl acetate. The pH of the buffer solution was adjusted to about 11 with 5N NaOH, forming a white precipitate which was collected by filtration and dried to give 2.06 g. (58% yield) of 20-DH-DO-20-[3-aza-bicyclo(3.2.2)nonan-3-yl]OMT. [Titration $pK_a$ values: 7.7 and 9.3; FDMS parent ion $(M^+ +1) = 707$].

EXAMPLE 2

20-DH-DO-20-Morpholino-OMT

Following the procedure outlined in Example 1, OMT (3.0 g., 5.0 mmoles), morpholine (0.87 ml., 10 mmoles), NaBH$_3$CN (0.31 g., 5 mmoles) and anhydrous MeOH (30 ml.) were reacted in the presence of molecular sieves (3A). Since a precipitate did not form when the pH of the buffer was adjusted to 11, the product was extracted from the buffer with CH$_2$Cl$_2$ to give 1.66 g. (50% yield) of 20-DH-DO-20-morpholino-OMT as a white foam. [Titration $pK_a$ values: 6.5, 8.4; FDMS parent ion $(M^+ +1) = 669$].

EXAMPLE 3

20-DH-DO-20-(4-Phenylpiperidin-1-yl)-OMT

OMT (5.97 g., 10 mmoles), 4-phenylpiperidine (3.22 g., 20 mmoles), NaBH$_3$CN (1.25 g., 20 mmoles) and methanol (60 ml.) were reacted using the procedure of Example 1, but substituting a pH 4.5 buffer for extraction, to give 3.7 g. of the title compound [FDMS parent ion $(M^+ +1) = 743$].

EXAMPLE 4

20-DH-DO-23-Deoxy-20,23-di(octahydroazocin-1-yl)-OMT 20,23-di-iodo-OMT (1.2 g., 1.5 mmoles) was dissolved in acetonitrile (20 ml.). Heptamethyleneimine (1.7 g., 1.9 ml., 15 mmoles) was added to this solution, and the reaction mixture was stirred at reflux for 1.5 hours. Volatiles were removed, and the resulting red oil was dissolved in CH$_2$Cl$_2$ (150 ml.). This solution was washed with saturated NaHCO$_3$ solution (100 ml.) and the CH$_2$Cl$_2$ phase was separated and dried over Na$_2$SO$_4$, filtered, and evaporated under vacuum. The residue obtained was subjected to flash column chromatography on silica gel 60 packed in MeOH/CH$_2$Cl$_2$ (1:9). The column was eluted stepwise with MeOH/CH$_2$Cl$_2$ as follows: 300 ml. of 1:9, 500 ml. of 1:4, 250 ml. of 3:7, 250 ml. of 2:3, 500 ml. of 1:1, and 500 ml. of 7:3. The desired fractions were combined to give 221 mg. (19% yield) of 20-DH-DO-23-deoxy-20,23-di(octahydroazocin-1-yl)-OMT as a white foam. [Titration $pK_a$ values: 6.9, 8.05, 8.9; FDMS parent ion $(M^+ +1) = 790$].

EXAMPLES 5–27

The following compounds can be prepared by the methods of the preceding examples.

20-DH-DO-20-(octahydroazocin-1-yl)DMT
20-DH-DO-20-(piperidin-1-yl)DMOT
20-DH-DO-20-(piperidin-1yl)DOMT
20-DH-DO-20-(4-hydroxypiperidin-1yl)DOMT
20-DH-DO-20-(decahydroazecin-1-yl)OMT
20-DH-DO-20-(octahydroazocin-1-yl)DOMT
20-DH-DO-20-(azacyclotridecan-1-yl)OMT
20-DH-DO-20-(hexahydroazepin-1-yl)DMT
20-DH-DO-20-(1,2,3,4-tetrahydroisoquinonlin-2-yl)OMT
20-DH-DO-20-(1,2,3,4-tetrahydroquinolin-1-yl)OMT
20-DH-DO-20-(azacycloundecan-1-yl)OMT
20-DH-DO-20-(4-methylpiperidin-1-yl)OMT
20-DH-DO-20-(pyrrolidin-1-yl)DMT
20-DH-DO-20-(octahydro-1H-azonin-1-yl)OMT
20-DH-DO-20-(octahydroazocin-1-yl)DMOT
20-DH-DO-20-(octahydroazocin-1-yl)DOMT
20-DH-DO-20-(4-phenylpiperidin-1-yl)DMT
20-DH-DO-20-(4-phenylpiperidin-1yl)-4'-deoxy-OMT
20-DH-DO-20-(decahydroazecin-1-yl)-4'-deoxy-OMT
20-DH-DO-20-(hexahydroazepin-1-yl)-4'-deoxy-OMT
20-DH-DO-20-(1,2,3,4-tetrahydroisoquinolin-2-yl)DOMT
20-DH-DO-20-(decahydrocyclopent[c]azepin-1-yl)OMT
20-DH-DO-20-(7-azabicyclo[2.2.1]heptan-1-yl)OMT
20-DH-DO-20-(3,5-dimethylpiperidin-1-yl)OMT
20-DH-DO-20-(3,5-dimethylpiperidin-1-yl)-4'-doxy-OMT
20-DH-DO-20-(3,4-dimethoxypiperidin-1-yl)OMT
20-DH-DO-23-deoxy-20,23-di(3,5-dimethylpiperidin-1-yl)OMT

EXAMPLE 28

Injectable Formulations (A) A formula 1 base is added to propylene glycol. Water and benzyl alcohol are added so that the solution contains 50% (by volume) propylene glycol, 4% (by volume) benzyl alcohol, and 200 mg/ml of a formula 1 base.

(B) A solution is prepared as described in Section A except that the solution contains 50 mg/ml of a formula 1 base.

(C) A solution is prepared as described in Section A except that the solution contains 350 mg/ml of a formula 1 base.

(D) A solution is prepared as described in Section A except that the solution contains 500 mg/ml of a formula 1 tartrate.

(E) A suspension is prepared by adding a finely ground formula 1 compound to carboxymethyl cellulose with thorough mixing so that the suspension contains 200 mg of the formula 1 base per ml of suspension.

We claim:

1. A compound of the formula

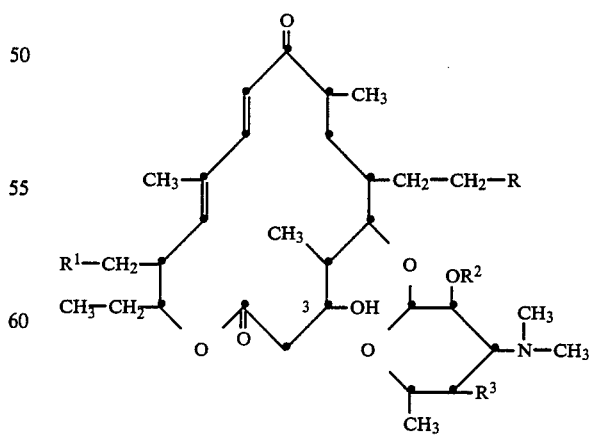

wherein
R is a saturated or unsaturated secondary amino group of the formula

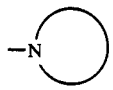

in which the nitrogen atom is part of an otherwise carbocyclic ring system selected from a monocyclic ring containing from 5 to 16 ring atoms or a bicyclic or tricyclic ring system containing from 8 to 20 ring atoms wherein one or more of the carbon atoms may be substituted by $C_1$–$C_4$ alkyl, $C_2$–$C_4$ alkenyl, $C_2$–$C_4$ alkynyl, $C_1$–$C_4$ alkoxy, $C_1$–$C_4$ alkoxycarbonyl, hydroxyl, $C_1$–$C_4$ alkanoyloxy, halo, halo-$C_1$–$C_4$ alkyl, —N($C_1$–$C_4$ alkyl)$_2$, —N(CH$_2$)$_m$,

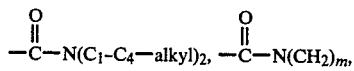

cyano, ethylenedioxy, benzyl, phenyl, or phenyl substituted by from 1 to 3 substituents selected from nitro, halo, $C_1$–$C_4$-alkyl, $C_1$–$C_4$ alkoxy, hydroxy, amino, or mono- or di-($C_1$–$C_4$ alkyl)amino; and m is an integer from 4 through 7;

$R^1$ is
(i) —OAr, —O—tetrahydrofuranyl, —O—tetrahydropyranyl, —SR$^5$, azido, —NR$^6$R$^7$, or N-phthalimido;
(ii) a saturated or unsaturated secondary amino group of the formula

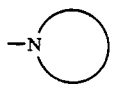

in which the nitrogen atom is part of an otherwise carbocyclic ring system selected from a monocyclic ring containing from 5 to 16 ring atoms or a bicyclic or tricyclic ring system containing from 8 to 20 ring atoms wherein one or more of the carbon atoms may be substituted by $C_1$–$C_4$ alkyl, $C_2$–$C_4$ alkenyl, $C_2$–$C_4$ alkynyl, $C_1$–$C_4$ alkoxy, $C_1$–$C_4$ alkoxycarbonyl, hydroxyl, $C_1$–$C_4$ alkanoyloxy, halo, halo-$C_1$–$C_4$ alkyl, —N($C_1$–$C_4$ alkyl)$_2$, —N(CH$_2$)$_m$,

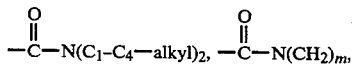

cyano, ethylenedioxy, benzyl, phenyl, or phenyl substituted by from 1 to 3 substituents selected from nitro, halo, $C_1$–$C_4$-alkyl, $C_1$–$C_4$ alkoxy, hydroxy, amino, or mono- or di-($C_1$–$C_4$ alkyl) amino; or
(iii) a monocyclic saturated or unsaturated nitrogen-containing heterocyclic ring bonded through the nitrogen atom, said ring having (1) from 5 to 7 ring atoms which include up to 3 additional heteroatoms selected from nitrogen, oxygen and sulfur, and (2) up to 3 substituent groups selected from methyl, ethyl and phenyl;

$R^2$ is hydrogen; $C_1$–$C_5$-alkanoyl which may have from one to three halo substituents; or benzoyl, phenylacetyl or phenylpropionyl which may have from one to five halo or methyl or from one to two methoxy, nitro or hydroxyl substituents;

$R^3$ is hydrogen; hydroxy; $C_1$–$C_5$-alkanoyloxy which may have from one to three halo substituents; benzoyloxy, phenylacetoxy or phenylpropionyloxy which may have from one to five halo or methyl or from one to two methoxy, nitro or hydroxyl substituents; or

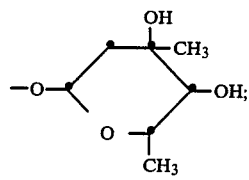

(mycarosyloxy)

Ar is
(i) phenyl, phenyl having from one to five halo, methoxyl or $C_1$–$C_4$-alkyl or from one to two nitro, amino, methylamino, ethylamino, dimethylamino, diethylamino, $C_4$–$C_{10}$-methyleneamino, azido, hydroxy, hydroxymethyl, aminomethyl, (methylamino)methyl, (ethylamino)methyl, (dimethylamino)methyl, (diethylamino)methyl, ($C_4$–$C_{10}$-methyleneamino)methyl, formyl, acetyl, benzoyl, methoxycarbonyl, ethoxycarbonyl, carboxamido, N-methylcarboxamido, N,N-dimethylcarboxamido, cyano, phenyl, phenoxy or benzyl substituents, or naphthyl;
(ii) a heteroaryl group selected from pyridinyl, pyrimidinyl, pyridazinyl, pyrazinyl, triazinyl, indolyl, isoquinolinyl, quinolinyl, quinazolinyl, cinnolinyl, quinoxalinyl, phthalazinyl benzotriazolyl, benzoxazolyl, benzimidazolyl, carbazolyl, or acridinyl which may have a $C_1$–$C_4$-alkyl, halo, methoxy, ethoxy, hydroxy (or the keto tautomer) or phenyl substituent;
(iii) $C_1$–$C_5$-alkanoyl which may have from one to three halo substituents; benzoyl, phenylacetyl, phenylpropionyl, phenoxyacetyl, phenylsulfonyl or phenylthioacetyl which may have from one to five halo or methyl or from one to two methoxy, nitro or hydroxyl substituents; methanesulfonyl; or trifluoromethanesulfonyl;

$R^5$ is $C_1$–$C_4$-alkyl which may have one or more fluoro or chloro substituents; cyclohexyl; phenyl, benzyl or phenethyl which may have from one to five halo or methyl or from one to two methoxy, nitro or hydroxyl substituents; or a heteroaryl group selected from imidazolyl, pyrazolyl, pyridinyl, pyrimidinyl, pyrazinyl, pyridazinyl, triazinyl, triazolyl, tetrazolyl, oxazolyl, isoxazolyl, oxadiazolyl, thiazolyl, isothiazolyl, thiadiazolyl, thienyl and furanyl which may have a $C_1$–$C_4$-alkyl, halo, methoxy, ethoxy, hydroxy (or the keto tautomer) or phenyl substituent;

$R^6$ is hydrogen; $C_1$–$C_6$-alkyl which may have one or more fluoro or chloro substituents, phenyl, benzyl, phenethyl or $C_3$–$C_8$-cycloalkyl; and $R^7$ is an $R^6$ group or $C_1$–$C_5$-alkanoyl which may have from one to three halo substituents; benzoyl, phenylacetyl, phenylpropionyl, phenoxyacetyl or phenylthioacetyl which may have from one to five halo or methyl of from one to two methoxy, nitro or hydroxyl substituents; or alkoxycarbonyl; one to two methoxy, nitro or hydroxyl substituents; or alkoxycarbonyl;

provided that (1) when $R^1$ is —$NHR^6$, $R^2$ must be hydrogen, $R^3$ must be hydrogen, hydroxy or mycarosyloxy, and Ar cannot be a type (iii) substituent; and (2) when $R^2$ is hydrogen, $R^3$ must be hydrogen, hydroxy or mycarosyloxy; and the acid addition salts thereof.

2. A compound of claim 1 wherein R is a saturated monocyclic ring.

3. A compound of claim 2 wherein the ring contains from 6 through 9 ring atoms.

4. A compound of claim 3 which has 6 ring atoms.

5. A compound of claim 4 wherein R is 3,5-dimethylpiperidino.

6. A compound of claim 3 which has 8 ring atoms.

7. A compound of claim 6 wherein R is octahydroazocin-1-yl.

8. A compound of claim 1 wherein R is a group (ii) substituent.

9. A compound of claim 8 wherein R is morpholino.

10. A compound of claim 8 wherein R is imidazol-1-yl.

11. A compound of claim 1 wherein R is a bicyclic or tricyclic ring system.

12. A compound of claim 11 wherein R is 3-azabicyclononan-3-yl.

13. A compound of claim 11 wherein R is 1,2,3,4-tetrahydroquinolin-1-yl.

14. A compound of claim 1 wherein $R^1$ is a group (i) substituent.

15. A compound of claim 14 wherein $R^1$ is —OAr.

16. A compound of claim 14 wherein $R^1$ is —$N(R^6)_2$.

17. A compound of claim 1 wherein $R^1$ is a group (ii) substituent.

18. A compound of claim 17 wherein $R^1$ is a saturated monocyclic ring containing from 6 through 9 ring atoms.

19. A compound of claim 1 wherein $R^1$ is a bicyclic or tricyclic ring system.

20. A compound of claim 19 wherein $R^1$ is 3-azabicyclononan-3-yl.

21. A compound of claim 1 wherein $R^3$ is hydrogen.

22. A compound of claim 1 wherein $R^3$ is hydroxy.

23. A compound of claim 1 wherein $R^2$ is hydrogen.

* * * * *